United States Patent [19]

Salonen

[11] Patent Number: 5,700,641
[45] Date of Patent: Dec. 23, 1997

[54] DIAGNOSTIC METHOD, TEST KIT, DRUG AND THERAPEUTIC TREATMENT FOR AUTOIMMUNE DISEASES

[76] Inventor: Eeva-Marjatta Salonen, Tunturikatu 15 B 46, FIN-00100 Helsinki, Finland

[21] Appl. No.: 396,238

[22] Filed: Mar. 1, 1995

[51] Int. Cl.$^6$ .......................... C12Q 1/68; G01N 33/564
[52] U.S. Cl. .......................... 435/6; 435/7.5; 435/7.95; 436/508; 436/513
[58] Field of Search .......................... 435/6, 7.4, 7.95, 435/7.5; 436/508, 513

[56] References Cited

FOREIGN PATENT DOCUMENTS 0276984  8/1988  European Pat. Off. .
9323572  11/1993  WIPO .

OTHER PUBLICATIONS

Herren Wu et al., "Building zinc fingers by selection: Toward a therapeutic application", Proc. Natl. Acad. Sci., vol. 92, Jan. 1995, pp. 344–348, Figure 1.
Gabibov Ag et al., "DNA–hydrolyzing autoantibodies", & Appl Biochem Biotechnol 1994, May–Jun.; 47(2–3): pp. 293–302, discussion 303, National Library of Medicine, file Medline.
S.M. Barbas et al., "Recognition of DNA by Synthetic Antibodies", J. Am. Chem. Soc, vol. 116, 1994: pp. 2161–2162.
Dialog Information Services, Derwent database WPI, Dialog accession No. 009259776, WPI accession No. 387189/47, Toshiba KK: "Method of detecting gene by reacting sample with antibody to single stranded oligo–nucleotide—of given base sequence, then detecting presence of antigen–antibody reaction", & JP, A, 4286957, 921012, 9247 (Basic).
National Library of Medicine, file Medline, NLM accession No. 95058242, Schriever–Schwimmer G. et al.: "Differentiation of micronuclei inmouse bone marrow cells: a comparison between CREST staining and fluorescent in situ hybridization with centromeric and telomeric DNA probes", Mutagenesis 1994, Jul.; vol. 9, pp. 333–340.
National Library of Medicine, file Medline, NLM accession No. 95347387, Herrmann M. et al.: "Preferential recognition of specific DNA motifs by anti–double–stranded DNA autoantibodies", & Eur. J. Immunol. 1995, Jul. vol. 25(7): pp. 1897–1904.
E.H. Blackburn, "The Molecular Structure of Centromeres and Telomeres", Ann.Rev Biochem. (1984) 53:163–94.
Virginia A. Zakian, "Structure and Function of Telomeres", Annu.Rev. Genet (1989) 23:579–604.
Elizabeth H. Blackburn, "Structure and Function of Telomeres", Nature.vol. 350. 18 Apr. 1991.
Robert K. Moyzis et al. "A Highly Conserved Repetitive DNA Sequence, (TTAGGG)n, Present at the Telomeres of Human Chromosomes", Proc.Natl.Acad.Sci.USA, vol.85, pp. 6622–6626, Sep. 1988.
Julianne Meyne et al. "Conservation of the Human Telomeres Sequence (TTAGGG)n, Among Vertebrates", Proc.Natl.Acad.Sci.USA, vol. 86, pp. 7049–7053, Sep. 1989.

Alan M. Weiner, "Eukaryotic Nuclear Telomeres: Molecular Fossils of the RNP World?", Cell, vol.52, 155–157, Jan. 29, 1988.
Guo–Liang Yu et al. "In Vivo Alteration of Telomeres Sequences and Senescence Caused by Mutated Tetrahymena Telomeres RNAs", Nature.vol. 344. Mar. 8, 1990.
Calvin B. Harley et al. "Telomeres Shorten During Ageing of Human Fibroblasts", Nature.vol. 345. 31 May 1990.
Shana M. Barbas et al. "Human Autoantibody Recognition of DNA".
John A. Mills, M.D., "Systemic Lupus Erythematosus", vol. 330 No.26, pp. 1871–1879.
Dennis M. Klinman."Polyclonal B Cell Activation in Lupus––Prone Mice Precedes and Predicts the Development of Autoimmune Disease", The Journal of Clinical Investigation, Inc. vol. 86, Oct. 1990, pp.1249–1254.
Dennis M. Klinman et al. "Development of the Autoimmune B Cell Repertorie in MRL–lpr/lpr Mice", The Journal of Immunology vol. 144 pp.506–511, No. 2, Jan. 15, 1990.
Salvador P. Casals et al. "Significance of Antibody to DNA in Systemic Lupus Erythematosus", Arthritis and Rheumatism, vol. 7, No.4 (Aug.), 1964 pp.379–390.
Marc C. Hochberg MD, MPH*, "Systemic Lupus Erthematosus", Rheumatic Disease Clinics of North American—vol. 16, No. 3, Aug. 1990, pp.617–639.
Chandra Mohan et al. "Nucleosome: A Major Immunogen for Pathogenic Autoantibody–Inducing T Cells of Lupus", J. Exp. Med., vol. 177 pp.1367–1381, May 1993.
Eng. M. Tan, "Antinuclear Antibodies:Diagnostic Markers for Autoimmune Diseases and Probes for Cell Biology", Advances in Immunology, vol. 44, pp.93–151.
Ajgswaak et al. "Predictive value of Complement Profiles and Anti–dsDNA in Systemic Lupus Erythematosus", Annuals of the Rheumatic Diseases, 1986: 45, 359–366.
E.J. Ter Borg, "Measurement of Increases in Anti–Double–Stranded DNA Antibody Levels as a Predictor of Disease Exacerbation in Systemic Lupus Erythematosus", Arthritis and Rheumatism, vol. 33, No. 5, May 1990 pp. 634–643.
Moshe Pistiner et al. "Lupus Erythematosus in the 1980s: A Survey of 570 Patents", Seminars in Arthritis and Rheumatism, vol. 21, No. 1 Aug. 1991: pp.55–64.
Ellen M. Ginzler, MD, MPH,* et al. "Outcome and Prognosis in Systemic Lupus Erythematosus", Rheumatic Disease Clinic of North American—vol. 14, No. 1, Apr. 1988 pp. 67–78.

*Primary Examiner*—David Saunders
*Attorney, Agent, or Firm*—Browdy and Neimark

[57] ABSTRACT

Synthesized telomeric sequences bind to and can be used for detecting anti-DNA antibodies in serum. Autoimmune diseases such as Lupus Erythematosus, Rheumatoid Arthritis, and Scleroderma, can be detected by detecting an elevated level of anti-DNA antibodies using telomeric sequences. Test kits for such detection are provided including immobilized telomeric sequences capable of binding anti-DNA antibodies. Pharmaceutical compositions for inhibiting or reducing the activity of anti-DNA antibodies contain an effective amount of telomeric sequences effective in inhibiting the antibodies specific to the patient treated.

26 Claims, No Drawings

DIAGNOSTIC METHOD, TEST KIT, DRUG AND THERAPEUTIC TREATMENT FOR AUTOIMMUNE DISEASES

FIELD OF INVENTION

The present invention relates to a method for detecting anti-DNA antibodies in samples obtained from living organisms, especially in mammalian serum, and more particularly to a diagnostic method for detecting anti-DNA-antibodies in serum from human beings and animals. The invention also relates to test kits for performing the said method and to a drug and a therapy for patients suffering from diseases involving the presence of anti-DNA-antibodies, specifically auto-immune disorders such as Lupus Erythematosus.

BACKGROUND OF THE INVENTION

Lupus erythematosus is an autoimmune disorder (antibodies are produced against self antigens), in which the body's immune system, for unknown reasons, attacks the connective tissue as though it were foreign, causing inflammation. Of the multitude of autoreactive antibodies that spontaneously arise during the disease, high levels of circulating autoantibodies to DNA are the best evidence of the pathogenesis.

In Systemic Lupus Erythematosus (SLE) there is almost invariable presence in the blood of antibodies directed against one or more components of cell nuclei. Certain manifestations in SLE seem to be associated with the presence of different antinuclear antibodies and genetic markers, which have suggested that SLE may be a family of diseases [Mills, J. A., Medical Progress 33, 1871-1879 (1994)].

The more common type of lupus erythematosus, Discoid Lupus Erythematosus (DLE), affects exposed areas of the skin. The more serious and fatal form, Systemic Lupus Erythematosus (SLE), affects many systems of the body, including the joints and the kidneys.

Animal models have confirmed that organ damage and premature death occurs only following the skewing of the B cell repertoire towards autoreactivity [Klinman, D. M. J. Clin. Invest. 86, 1249-1254 (1990). Klinman, D. M. et al., J. Immunol. 144, 506-511 (1990)]. Lupus nephritis, especially diffuse proliferative glomerulonephritis, has been known to be associated with circulating antibodies to double stranded (native) DNA [Casals, S. et al., Arthritis Rheum. 7, 379-390 (1964); Tan E. M. et al., J. Clin. Invest. 82, 1288-1294 (1966)]. The detection of antinuclear antibodies is a sensitive screening test for SLE. Antinuclear antibodies occur in more that 95% of patients [Hochberg, M. C. Rheum. Dis. Clin. North Am. 16, 617-39 (1990)].

The most common antibody in patients with SLE is directed against nucleosomal DNA-histone complexes, and it yields a homogeneous staining pattern on the immunofluorescence test for antinuclear antibodies [Mohan, C. et al., J. Exp. Med. (1993) 177, 1367-81]. Antinuclear antibodies are also seen in most of the other rheumatic diseases, [Tan, E. M., Adv. Immunol. (1989) 44, 93-151] and are produced transiently in viral infections and are present, usually in low titers, in about 2 percent of the normal population.

Antibodies to native or double-stranded DNA and to Sm, a ribonuclear protein antigen, are more specific than other antinuclear antibodies for the diagnosis of SLE. [Mills, J. A., Medical Progress 33, 1871-1879 (1994)]. It is more common to have nephritis in patients with antinative DNA, the titer of this antibody being a useful measure of disease activity [Swaak, A. J. G. et al., Ann. Rheum. Dis. 1986, 45: 359-66; ter Borg, E. J. et al., Arthritis Rheum. 1990: 33, 634-43].

The 10-year average survival rate from diagnosis for patients with SLE observed over the past decade approaches 90 percent [Pistiner et al., Semin. Arthritis Rheum. 1991: 21, 55-64; Ginzler et al., Rheum. Dis. Clin. North Am. 1988: 14, 67-78].

During 1993-1994 the present inventor was working at the Scripps Research Institute in a project involving a human antibody gene library from a Systemic Lupus Erythematosus (SLE) donor. The library was panned against human placental DNA (a commercial product), and selected monoclonal antibodies were tested for human antibody recognition of DNA. The results of the project are in press [Barbas, S. M., Ditzel, H. J., Salonen, E.-M., Yang, W.-P., Silverman, G. J. and D. R. Burton, Human autoantibody recognition of DNA, Proc. Natl. Acad. Sci. (1995)]. The object was to discover a specific sequence of DNA that would be recognized by a human SLE autoantibody.

A haploid set of human chromosomes (haploid human genome) is composed of the estimated 3 billion ($3 \times 10^9$) bp of DNA. The probability of finding, experimentally, a short sequence that is recognized by autoantibodies is small. Thus, despite a vast amount of work, a functionally correct sequence has not been found.

SUMMARY OF THE INVENTION

Now the present inventor, having considered the matter and having made further studies and investigations has surprisingly found that synthesized telomeric sequences, i.e. sequences that are found at the terminal ends of the chromosomes bind the autoantibodies in question and that they can be used to detect and to inhibit said autoantibodies.

It is therefore an object of the present invention to provide a method for detecting anti-DNA-antibodies in eukaryotic samples.

More specifically, it is an object of the invention to provide a method for detecting anti-DNA-antibodies in serum from mammals, especially human beings.

It is a further object of the invention to provide a diagnostic method for the detection of Lupus Erythematosus, Rheumatoid Arthritis, Scleroderma and other autoimmune diseases, especially Systemic Lupus Erythematosus in mammals, by detecting, with the aid of telomeric sequences specific to said mammal, an elevated level of anti-DNA-antibodies in the serum of said mammal.

In the following specification and claims the term "telomeric sequence" used generally in context with the invention should be understood as meaning any of the telomeric sequences of DNA selected from the group consisting of a single stranded telomere, a complementary strand thereto, a double stranded telomere, and a part or a repeat or a combination of any of the foregoing, which is capable of binding said anti-DNA-antibodies.

It is also an object of the invention to provide a test kit for detecting anti-DNA-antibodies, said test kit preferably including immobilized telomeric sequences capable of binding to anti-DNA-antibodies. The test kit preferably includes a label indicating the binding of autoantibody to telomeric sequence.

It is a further object of the invention to provide a drug capable of inhibiting or reducing the activity of anti-DNA-antibodies in patients suffering from autoimmune disorders, which drug contains an amount of telomeric sequences effective in inhibiting the patients specific autoantibodies.

It is a further object of the invention to provide a method useful in the treatment of autoimmune disorders by reducing or inhibiting the activity of anti-DNA-antibodies in a mammalian system by administering to said mammal an effective amount of a telomeric sequence or an agent containing a telomeric sequence or a functional part thereof, which results in significant inhibition of the autoantibodies in said mammal.

Telomeres, terminal DNA-protein complexes of chromosomes, are essential in the protection, positioning and for the stability of chromosomes [E. H. Blackburn and J. W. Szostak, Annu. Rev. Biochem. 53, 163 (1984); V. A. Zakian, Annu. Rev. Genet. 23, 579 (1989)]. They also are required for the complete replication of the chromosomal terminus during each cell cycle. All known eukaryotic telomeres consist of hundreds to thousands of simple, repeated tandem sequences of DNA and associated proteins. A functional human telomere is defined as having a repeat of the sequence TTAGGG [E. H. Blackburn, Nature 350, 569 (1991); R. K. Moyzis et al., Proc. Natl. Acad. Sci. U.S.A. 85, 6822 (1988); J. Meyne et al. Proc. Natl. Acad. Sci. U.S.A, 86, 7049 (1989)]. A general structure of repeated sequences of G- and C-rich complementary strands of the eukaryotic telomeres is $(T \text{ or } A)_m(G)_n$ [Blackburn, E. H. and Szostak, J. W. Annu. Rev. Biochem. 53, 163–194 (1984); Weiner, A. M. Cell 52, 155–157 (1988)].

Telomeres can be visualized at the tips of the chromosomes using a fluorescence microscope. When labeled $(GGGTTA)_7.(TAACCC)_7$ oligomers were hybridized to metaphase chromosomes using a biotin-avidin detection method the distinct, speckled fluorescent signal was distinctly seen at the chromosomal ends [Meyne, J. M. et al., Proc. Natl. Acad. Sci. 86, 7049–7053 (1989)]. Although telomeric sequences are highly conserved in evolution, the correct sequence of the telomeric repeat is required for telomere function, since, for example, addition of telomeric DNA harboring a mutated telomeric sequence to the ends of the endogenous Tetrahymena telomeres (having a sequence repeat 5'-TTGGGG-3') leads to telomere length instability and death [Yu et al., Nature (London) 344, 128–132 (1990); Harley, C. B. et al., Nature (London) 345, 458–460 (1990)].

The structure and function of telomeres has been described by E. H. Blackburn, Nature, 350, 569–573 (1991). Telomeres have not been reported as having any connection with SLE or other autoimmune diseases.

For better understanding of the present invention, together with other and further objects and the nature and advantages of the invention, reference is made to the following detailed description of specific embodiments.

DETAILED DESCRIPTION OF THE INVENTION

The present invention is based on the novel finding that human autoantibodies (anti-DNA-antibodies) are recognized and bound by telomeres. In accordance with the present invention, a method is disclosed for the detection of autoantibodies or anti-DNA-antibodies in samples of eukaryotic origin, especially mammalian serum.

Telomeres are evolutionally highly conserved in nature and all eukaryotic beings have telomeres of a very closely related structure. The human telomere has a repeat of the sequence 5'-TTAGGG-3'. Other eukaryotic telomeres have very similar sequences, usually only one nucleotide in the hexapeptide is different. Thus, the method is applicable on humans and animals alike.

It is also possible to use parts of the telomere that recognize the autoantibodies. Thus a part of the hexanucleotide repeat, such as the CCC terminal end, may be used for performing the recognition.

It has been found that the anti-DNA-antibodies in some samples may bind more specifically to one or the other of the complementary single stranded sequences, while some bind more readily to a double stranded telomeric DNA (ds DNA).

The telomeric sequence used in the present invention is either the single stranded telomere sequence, which for humans is 5'-TTAGGG-3', its complementary sequence (for humans 3'-AATCCC-5'), a functional part of any of the above, an oligonucleotide having two or more repeats of the telomeric or complementary sequence, a double stranded DNA formed of the above single stranded sequences or an oligonucleotide part thereof or repeats of the telomeric doublet.

In the method for detecting anti-DNA-antibodies according to the present invention, the selected functional telomeric sequence is synthetized in a way known to those skilled in the art, e.g. in commercial nucleotide synthetizers. The obtained sequence is then preferably immobilized on a carrier, which may comprise the walls of microtiter wells, plastic beads, porous sheets, etc. which carriers are well known to those skilled in the art. The telomeric sequence may also be labeled in ways detectable in known types of immunoassays.

When an immobilized telomeric sequence is contacted with a sample to be tested, any anti-DNA-antibodies present in the sample will attach to the immobilized sequence. The complex formed in the binding reaction may be detected by means well known in the art of immunochemistry. Thus, if the complex is contacted with labeled secondary antibodies, the immunoglobulin part thereof which will attach to the bound autoantibody.

The autoantibodies recognized by the telomeric sequences may be of different immunoglobulin classes, which may indicate so far unknown differences in disease or disease pattern. Thus, the autoantibodies may be either IgG, IgM, IgA, IgD, or IgE class, since the autoantibodies can belong to any of the known immunoglobulin classes.

Different anti-Ig antibodies will detect the presence of the different Ig class autoantibodies. Thus, for example, labeled anti-IgG will be used to determine the presence of the IgG class autoantibodies, anti-IgM antibody will be used for detecting the IgM class autoantibodies, and so on.

It is known in the art that SLE patients have predominantly IgG class autoantibodies, while for instance rheuma patients seem to have a predominance of IgM autoantibodies. However, the tests performed in connection with the present invention show that SLE patients often have both IgG and IgM class autoantibodies, the level IgG class autoantibodies being elevated in all tested patients (17) with SLE compared to SLE negative patients.

The amount of bound autoantibody can be detected with the aid of the label on the anti-Ig antibody used in a way known in the art and depending on the label, the immunoassay, etc. The label may be a radio label, an enzyme label, a fluorochrome label, a dye, a sol, biotin, a luminescent label and/or a labeled polyclonal or monoclonal antibodies or the like. The assay may be an EIA, radioimmunoassay, immunofluorescent assay, immunochromatographic assay or any other that is designed to detect autoantibody binding of a telomeric DNA.

The tests performed in connection with the present invention very conclusively show that a diagnosis of lupus erythematosus patients can be performed using a telomeric sequence for the autoantibody recognition. Out of 17 SLE patients all were diagnosed positive in the IgG class autoantibody binding when tested with the assays of the present invention. The test is easy to perform, it is quick and reliable. The need for this kind of test is enormous in the art, since previously the testing for SLE has been uncertain and tedious. In actual fact no certain diagnosis has been possible until clear signs of serious disorders have appeared.

The tests performed so far also suggest that rheumatic patients may be diagnosed, especially by detecting the presence of the IgM class autoantibodies.

In systemic lupus erythematosus (SLE) the serum of the patient almost invariably contains antibodies directed against the cell nuclei. Some of these are directly responsible for the disorders caused by the disease. According to the invention it has been found that telomeric sequences bind these autoantibodies and inactivate them.

The telomeric sequences, parts or repeats thereof, single or double stranded used in the above described assays may thus also be used as active components in drugs against the destructive activity of the autoantibodies in patients suffering from diseases and/or disorders caused by or involving the presence of autoantibodies.

More specifically, the active part of the drug is a single or double stranded telomeric sequence, a repeat or a part thereof, a complementary sequence or a combination of any of the foregoing, (referred to generally as a telomeric sequence) which is recognized by a patient autoantibody. A drug according to the present invention thus comprises an amount of a telomeric sequence, as defined above, which is effective to inhibit or reduce the activity of the patient's autoantibodies.

The present invention comprises drugs for humans as well as veterinary preparations containing telomeric sequences specific to the mammal in question.

Moreover, the present invention makes it possible to give the patient in question precisely the telomeric sequence that will be most effective to the patient's own autoantibodies. The patient can first be tested with an assay according to the present invention so as to determine which telomeric sequence will best bind to the autoantibodies. Thus, assays will determine whether single or double stranded telomeric sequences should be used, and which Ig class the patient's antibodies are.

In the preferred therapeutic embodiment of the present invention the regimen for therapy is designed individually to each patient based on their autoantibody binding, i.e which immunoglobulin class, IgG, IgM etc., and which telomeric form they prefer.

The amount of active telomeric agent that should be given to a patient will vary with the patient's race, age, illness, etc. and the most effective dose will have to be determined on a case by case basis. However, the telomeres are DNA sequences existing as such in the chromosomes and thus they are part of the human body. Thus, it is not believed that the maximum amount of telomere given to a patient will be critical.

The telomeric sequences of the present invention may be formulated into pharmaceutical preparations such as injectable solutions in a way known in the pharmaceutical art.

The following Examples illustrate the invention without, however, limiting it in any way.

EXAMPLE 1

Synthesis of Telomeric Sequences

Synthesis of oligonucleotides was carried out by a commercial apparatus, Oligonucleotide Synthesizer (Applied Biosystems). The following oligonucleotides were synthetized:

Order number 2667: 5'-TTAGGG TTAGGG TTAGGG TTAGGG TTAGGG-3' (SEQ ID NO:1)

Order number 2668: 5'-CCCTAA CCCTAA CCCTAA CCCTAA CCCTAA-3' (SEQ ID NO:2)

A duplex DNA was formed in the laboratory as follows:

A volume of 50 µl (50 µg) of each oligo (2667 and 2668) in 10 mM Tris–1 mM EDTA containing 50 mM NaCl, pH 7.4 buffer were combined and heated for 5 min at 75° C. The mixture was left to cool at room temperature for an hour. The cooled mixture was immediately coated on polystyrene microtiter wells (Nunc) in a concentration of 1 or 2 µg per ml phosphate-buffered saline (PBS, pH 7.4). Each well received 100 µl of coating solution.

EXAMPLE 2

Assays for Autoantibody Detection

1. Polystyrene microtiter wells were coated with the single stranded oligonucleotides 2667 or 2668 or with the duplex DNA (2667+2668) obtained in Example 1. The coating concentration was 1 or 2 µg per ml PBS, pH 7.4. The coating volume was 100 µl. The plates were incubated at 37° C. without cover until dry.

2. The plates were washed three times with 10 mM PBS. pH 7.4 containing 0.05% Tween 20 (Fluka Ag).

3. Postcoating was carried out by applying a volume of 100 µl of Dulbecco buffer containing 0.5% bovine serum albumin (BSA) per well to block the nonspecific binding. The incubation took one hour at 37° C. under plastic adhesive cover to prevent the differential evaporation.

4. The plates were washed as in 2 and dried, and stored at +4° C. for later use.

EXAMPLE 3

The Detection of Autoantibodies Against Telomeric Sequences

1. Serum from diagnosed SLE patients and healthy controls were diluted 1:10 in Dulbecco's buffer containing 0.5% BSA and 0.05% Tween 20 and a volume of 100 µl of the serum dilution was incubated for two hours at 37° C. in the coated wells under plastic adhesive cover.

2. The plates were washed three times with 10 mM PBS. pH 7.4 containing 0.05% Tween 20 (Fluka Ag).

3. A volume of 100 µl of alkaline phosphatase-labeled swine anti-human IgG (for IgG class autoantibody determination) or alkaline phosphatase labeled swine anti-human IgM (for IgM class autoantibody determination) diluted 1:200 in Dulbecco's buffer containing 0.5% BSA and 0.05% Tween 20.

The incubation took place for one hour at 37° C.

4. The plates were washed as in 2.

5. A volume of 100 µl of substrate, 0.2% paranitrophenyl phosphate disodium salt in diethanolamine buffer was added per well, and the plates were incubated for 30 min at room temperature.

6. A volume of 100 µl of 1M sodium hydroxide (NaOH) was added per well to stop the reaction.

7. The wells were recorded using a Titertek Multiscan spectrophotometer using the wavelength 405 nm.

The results of the test are indicated in Tables 1 and 2.

TABLE 1

SLE-patient assays

| Patient | IgG-class autoantibody | | | IgM-class autoantibody | | |
|---|---|---|---|---|---|---|
| | 2667 | 2668 | 2667 + 2668 | 2667 | 2668 | 2667 + 2668 |
| 1. | 0.158 | 0.524 | 0.166 | 1.134 | 1.132 | 1.118 |
| | 0.152 | 0.449 | 0.093 | 1.167 | 1.132 | 1.119 |
| 2. | 0.095 | 0.268 | 0.132 | 0.017 | 0.782 | 0.119 |
| | 0.095 | 0.237 | 0.119 | 0.012 | 0.700 | 0.110 |
| 3. | 0.278 | 1.456 | 0.661 | 0.055 | 0.225 | 0.090 |
| | 0.308 | 1.299 | 0.584 | 0.051 | 0.228 | 0.092 |
| 4. | 0.434 | 0.699 | 0.185 | 0.058 | 0.200 | 0.113 |
| | 0.419 | 0.700 | 0.165 | 0.057 | 0.190 | 0.106 |
| 5. | 0.173 | 0.442 | 0.223 | 0.215 | 1.033 | 0.351 |
| | 0.201 | 0.393 | 0.217 | 0.201 | 1.092 | 0.352 |
| 6. | 0.077 | 0.833 | 0.276 | 0.045 | 0.330 | 0.161 |
| | 0.088 | 0.615 | 0.248 | 0.041 | 0.299 | 0.160 |
| 7. | 0.257 | 0.201 | 9.186 | 0.034 | 0.189 | 0.048 |
| | 0.264 | 0.208 | 0.156 | 0.035 | 0.189 | 0.048 |
| 8. | 0.090 | 0.058 | 0.042 | 0.039 | 0.116 | 0.037 |
| | 0.106 | 0.083 | 0.030 | 0.040 | 0.093 | 0.033 |
| 9. | 0.559 | 1.082 | 0.708 | 0.030 | 0.244 | 0.064 |
| | 0.639 | 0.991 | 0.632 | 0.026 | 0.209 | 0.061 |
| 10. | 0.093 | 0.069 | 0.035 | 0.038 | 0.253 | 0.079 |
| | 0.104 | 0.065 | 0.029 | 0.029 | 0.225 | 0.074 |
| 11. | 0.033 | 0.120 | 0.034 | 0.211 | 0.731 | 0.376 |
| | 0.022 | 0.090 | 0.036 | 0.233 | 0.802 | 0.383 |
| 12. | 0.359 | 0.908 | 0.284 | 0.020 | 0.219 | 0.083 |
| | 0.394 | 0.852 | 0.262 | 0.038 | 0.251 | 0.079 |
| 13. | 0.047 | 0.136 | 0.038 | 0.038 | 0.507 | 0.122 |
| | 0.031 | 0.076 | 0.032 | 0.123 | 0.536 | 0.129 |
| 14. | 0.061 | 0.184 | 0.059 | 0.163 | 1.317 | 0.396 |
| | 0.046 | 0.137 | 0.054 | 0.168 | 1.573 | 0.416 |
| 15. | 0.822 | 0.918 | 1.154 | 0.039 | 0.116 | 0.037 |
| | | | | 0.040 | 0.093 | 0.033 |
| 16. | 0..086 | 0.628 | 0.073 | | | |
| 17. | 1.794 | 1.832 | 1.597 | | | |

TABLE 2

Control assays (no SLE-diagnosis)

| Patient | IgG-class autoantibody | | | IgN-class autoantibody | | |
|---|---|---|---|---|---|---|
| | 2667 | 2668 | 2667 + 2668 | 2667 | 2668 | 2667 + 2668 |
| A. | 0 | 0.001 | 0.004 | 0.014 | 0.146 | 0.058* |
| B. | 0.024 | 0.005 | 0.002 | 0.006 | 0.056 | 0.023* |
| | 0.001 | 0.018 | 0.004 | 0.016 | 0.074 | 0.039* |
| C. | 0 | 0 | 0 | 0.005 | 0.121 | 0.058** |
| | 0 | 0 | 0 | 0.021 | 0.165 | 0.078** |
| D. | 0.002 | 0.002 | 0.005 | 0 | 0.042 | 0.025* |
| | 0 | 0 | 0.002 | 0.006 | 0.060 | 0.047* |
| E. | 0.002 | 0 | 0 | 0 | 0 | 0.008* |
| | 0 | 0 | 0.062 | 0.009 | 0.025 | 0.018* |
| F. | 0.001 | 0.003 | 0 | 0 | 0.050 | 0.029* |
| | 0.002 | 0 | 0 | 0.003 | 0.082 | 0.033* |
| G. | 0.005 | 0.003 | 0.002 | 0 | 0 | 0.004 |
| | 0.005 | 0 | 0.001 | 0.004 | 0.005 | 0.010 |

Note:
2667 and 2668 comprise single stranded telomeric DNA
2667 + 2668 comprises double stranded DNA
*Patients with suspected viral infection from the diagnostic routine
**Patients C was born in 1992

The above results clearly show that the serum of SLE patients demonstrate a high level of anti-DNA-antibodies binding to the telomeric sequences while normal control individuals have a significantly lower level, almost negligible in the IgG class. The present assay can thus be used for screening SLE.

EXAMPLE 4

Inhibition of Autoantibody Binding to Immobilized Telomeric Sequences

To provide proof that the binding is specific and that the antibodies can be neutralized with the specific telomeric sequence, the assay was performed as described above in Example 3 with the following modification. An amount of 5 µg/ml of oligonucleotide 2667, 2668 or the duplex DNA (2667+2668), respectively, was added to a 1:25 dilution of patient serum and incubated for at room temperature. After this incubation a volume of 100 µl of each incubation was added per well coated with the identical telomeric sequence (as in Example 2). Incubation lasted for 2 hours at 37° C., and the IgG or IgM class autoantibody binding was assayed using the corresponding labeled swine anti-IgG anti-IgM antibodies, respectively as in Example 3. The same patient serum diluted 1:25 without an addition of telomeric sequence served as a control.

The results are shown in Table 3.

TABLE 3

Inhibition of IgG class autoantibody binding to immobilized telomeric sequences by the telomeric sequence indicated in the Table.

| SLE No. | without inhibitor | inh. 2667 | inh. 2668 | inh. 2667 + 2668 |
|---|---|---|---|---|
| | Immobilized sequence 2667 | | | |
| 1. | 1.840 | 0.037 | 0.151 | 0.035 |
| | 1.736 | 0.036 | 0.201 | 0.0221 |
| 2. | 0.320 | 0.042 | 0.030 | 0.009 |
| | 0.300 | 0.045 | 0.048 | 0.029 |
| | Immobilized sequence 2665 | | | |
| 1. | 1.131 | 0.186 | 0.036 | 0.077 |
| | 0.963 | 0.101 | 0.022 | 0.075 |
| 2. | 0.829 | 0.027 | 0.031 | 0.064 |
| | 1.035 | 0.034 | 0 | 0.039 |
| | Immobilized sequence 2667 + 2668 | | | |
| 1. | 1.047 | 0.179 | 0.133 | 0.098 |
| | 1.134 | 0.163 | 0.142 | 0.070 |
| 2. | 0.223 | 0.042 | 0.027 | 0.031 |
| | 0.270 | 0.045 | 0.040 | 0.031 |

Inhibition of IgM class autoantibody binding to immobilized telomeric sequences by the telomeric sequences indicated in the Table.

| SLE No. | without inhibitor | inh. 2667 | inh. 2668 | inh. 2667 + 2668 |
|---|---|---|---|---|
| | Immobilized sequence 2667 | | | |
| 1. | 0.244 | 0.078 | 0.046 | 0.029 |
| | 0.214 | 0.061 | 0.029 | 0.051 |
| 2. | 0.119 | 0.029 | 0.018 | 0.032 |
| | 0.153 | 0.039 | 0.100 | 0.053 |
| | Immobilized sequence 2668 | | | |
| 3. | 0.487 | 0.119 | 0.071 | 0.170 |
| | 0.489 | 0.139 | 0.011 | 0.125 |
| 4. | 0.289 | 0.053 | 0 | 0.073 |
| | 0.278 | 0.147 | 0 | 0.073 |
| | Immobilized sequence 2667 + 2668 | | | |
| 1. | 0.355 | 0.101 | 0.059 | 0.078 |
| | 0.292 | 0.106 | 0.049 | 0.097 |

| SLE No. | without inhibitor | inh. 2667 | inh. 2668 | inh. 2667 + 2668 |
|---|---|---|---|---|
| 2. | 0.074 | 0.121 | 0.020 | 0.012 |
|  | 0.075 | 0.068 | 0.064 | 0.060 |

The above test results show that the telomeric sequences are capable of binding to autoantibodies present in serum in vitro. This clearly implies that said telomeric sequences are capable of inhibiting the autoantibody binding site also in vivo. The telomeric sequences are therefore proposed for being used as specific therapeutic agents in patients suffering from autoimmune diseases which include the presence of autoantibodies in the body fluid of said patient.

EXAMPLE 5

Inhibition of IgG Class Autoantibody Binding to Parts of the Telomeric Sequence

The test of Example 4 was repeated for the partiel sequences GGG and CCC, respectively. The results are shown in the Table below.

| Patient no. | without inhibitor | inh. GGG | inh. CCC |
|---|---|---|---|
| Immobilized sequence 2667 | | | |
| 3. | 0.600 | 0.528 | 0.245 |
| 4. | 0.327 | 0.281 | 0.198 |
| Immobilized sequence 2668 | | | |
| 3. | 0.765 | 0.734 | 0.528 |
| 4. | 0.943 | 0.875 | 0.807 |

| Patient no. | without inhibitor | inh. GGG | inh. CCC |
|---|---|---|---|
| Immobilized sequence 2667 +2868 | | | |
| 3. | 0.372 | 0.323 | 0.323 |
| 4. | 0.147 | 0.121 | 0.143 |

The results indicate that some binding also takes place to parts of the telomeric sequence.

EXAMPLE 6

Pharmaceutical Preparation

A pharmaceutical preparation is pepared from the telomeric sequence 2667: 5'-TTAGGG TTAGGG TTAGGG TTAGGG TTAGGG-3' (SEQ ID NO:1) by dissolving 1 µg/ml of said sequence in physiological buffer. The solution is stored at 4° C. under sterile conditions.

PROPHETIC EXAMPLE IN VIVO

Administering a Telomeric Sequence to an SLE Patient

The serum from a patient is diagnosed with an assay according to the invention. Said serum is found to contain an elevated amount of autoantibodies of the IgG class binding predominantly to the telomeric sequence 2667 of Example 1.

The telomeric sequences 2667 as prepared in Example 5 is administered to said patient intravenously at a dose of 100 ml during three consequtive days. After one further day the serum of said patient is found to contain significantly less of said autoantibodies.

I claim:

1. A method for detecting anti-DNA-antibodies in a sample by contacting said sample with a telomeric sequence of DNA selected from the group consisting of a single stranded telomere, a complementary strand thereto, a double stranded teleomere, and a part or a repeat or a combination of any of the foregoing, to provide binding of said antibodies to said telomeric sequence of DNA, and detecting said binding of said antibodies to said telomeric sequence.

2. The method according to claim 1, wherein the telomeric sequence is selected from the group consisting of the human telomere strand 5'-TTAGGG-3', the complementary strand thereto, a double stranded human telomere, a functional part of any of said strands, a repeat of any of said strands and a combination of any of the foregoing.

3. The method according to claim 2, wherein said repeat of said telomere strand is selected from the group consisting of

5'-TTAGGG TTAGGG TTAGGG TTAGGG TTAGGG-3' (SEQ ID NO:1)

5'-CCCTAA CCCTAA CCCTAA CCCTAA CCCTAA-3' (SEQ ID NO:2), and a duplex thereof.

4. The method according to claim 1 said sample is mammalian serum.

5. The method according 4, wherein the serum is human serum.

6. A diagnostic method for detecting autoimmune diseases in mammals by contacting a serum sample from said mammal with telomeric sequence of DNA which is specific to said mammal and which is selected from the group consisting of a single stranded telomere, a complementary strand thereto, a double stranded telomere, a part or a repeat or a combination of any of the foregoing, to detect an elevated level of autoantibodies present in said mammals above a normal level of autoantibodies.

7. The diagnostic method of claim 6 wherein said autoimmune disease is selected from the group consisting of Lupus Erythematosus, Rheumatoid Arthritis and Scleroderma.

8. The diagnostic method of claim 7 wherein said autoimmune disease is Systemic Lupus Erythematosus (SLE).

9. The diagnostic method according to claim 6, wherein said telomeric sequence is selected from the group consisting of the human telomere strand 5'-TTAGGG-3', the complementary strand thereto, a double stranded human telomere, a functional part of any of said strands, a repeat of any of said strands and a combination of any of the foregoing.

10. The diagnostic method according to claim 9, wherein said repeat of said telomere strand is selected from the group consisting of

5'-TTAGGG TTAGGG TTAGGG TTAGGG TTAGGG-3' (SEQ ID NO:1)

5'-CCCTAA CCCTAA CCCTAA CCCTAA CCCTAA-3' (SEQ ID NO:2), and a duplex thereof.

11. The diagnostic method of claim 6, wherein the immunoglobulin (Ig) class of said autoantibodies is determined with the aid of anti-Ig-antibodies.

12. The diagnostic method according to claim 9, wherein the existence of SLE in a human patient is detected by contacting a sample of said patient's serum with an immobilized human telomeric sequence to bind autoantibodies present in said serum to said immobilized telomeric sequence and detecting an elevated level of bound IgG class autoantibodies among said bound autoantibodies.

13. The diagnostic method according to claim 9, wherein the existence of SLE in a human patient is detected by contacting a sample of said patient's serum with an immobilized human telomeric sequence to bind autoantibodies present in said serum to said immobilized telomeric sequence and detecting an elevated level of bound IgM class autoantibodies among said bound autoantibodies.

14. A test kit for the diagnosis of autoimmune disease in mammals, said test kit including a telomeric sequence of DNA selected from the group consisting of a single stranded telomere, a complementary strand thereto, a double stranded telomere, a part or a repeat or a combination of any of the foregoing, capable of binding autoantibodies present in said serum, wherein said telomeric sequence is immobilized on a solid support and a label capable of indicating the binding of said autoantibody to said telomeric sequence.

15. The test kit according to claim 14 wherein said telomeric sequence is selected from the group consisting of the human telomere strand 5'-TTAGGG-3', the complementary strand thereto, a double stranded human telomere, a functional part of any of said strands, a repeat of any of said strands and a combination of any of the foregoing.

16. The test kit according to claim 15, wherein said repeat of said telomere strand is selected from the group consisting of

5'-TTAGGG TTAGGG TTAGGG TTAGGG TTAGGG-3' (SEQ ID NO:1)

5'-CCCTAA CCCTAA CCCTAA CCCTAA CCCTAA-3' (SEQ ID NO:2), and a duplex thereof.

17. The test kit according to claim 14, wherein said kit further comprises a labeled telomeric sequence.

18. The test kit according to claim 14 wherein said label is selected from the group consisting of a radio label, an enzyme label, a fluorochrome label, a dye, a sol, biotin, and a luminescent label.

19. The test kit according to claim 14, wherein the label is provided as one or more labeled anti-Ig-antibodies selected from the group consisting of anti-IgG, anti-IgM, anti-IgA, anti-IgD, and anti-IgE.

20. The test kit according to claim 19 wherein said anti-Ig antibody is anti-IgG or anti-IgM.

21. A test kit for the diagnosis of autoimmune disease in mammals, said test kit including a telomeric sequence of DNA selected from the group consisting of a dingle stranded telomere, a complementary strand thereto, a double stranded telomere, a part or a repeat or a combination of any of the foregoing, capable of binding autoantibodies present in said serum; and an amount of one or more labelled anti-Ig-antibodies selected from the group consisting of anti-IgG, anti-IgM, anti-IgA, anti-IgD and anti-IgE.

22. The test kit according to claim 21, wherein said telomeric sequence is immobilized on a solid support.

23. The test kit according to claim 21 wherein said telomeric sequence is selected from the group consisting of the human telomere strand 5'-TTAGGG-3', the complementary strand thereto, a double stranded human telomere, a functional part of any of said strands, a repeat of any of said strands, and a combination of any of the foregoing.

24. The test kit according to claim 23 wherein said repeat of said telomere strand is selected from the group consisting of

5'-TTAGGG TTAGGG TTAGGG TTAGGG TTAGGG-3'
SEQ ID NO:1

5'-CCCTAA CCCTAA CCCTAA CCCTAA CCCTAA-3'
SEQ ID NO:2 and a duplex thereof.

25. The test kit according to claim 21 wherein said label is selected from the group consisting of a radio label, an enzyme label, a fluorochromic label, a dye, a sol, biotin, and a luminescent label.

26. The test kit according to claim 21 wherein said anti-Ig-antibody is anti-IgG or anti-IgM.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

TTAGGGTTAG GGTTAGGGTT AGGGTTAGGG    30

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

CCCTAACCCT AACCCTAACC CTAACCCTAA    30